(12) United States Patent
Hoehmann et al.

(10) Patent No.: US 10,436,714 B2
(45) Date of Patent: Oct. 8, 2019

(54) DETECTING DAMAGE TO A CONVERTER DEVICE

(71) Applicant: OSRAM GmbH, Munich (DE)

(72) Inventors: Peter Hoehmann, Berlin (DE); Stefan Hadrath, Falkensee (DE)

(73) Assignee: OSRAM GMBH, Munich (DE)

( * ) Notice: Subject to any disclaimer, the term of this patent is extended or adjusted under 35 U.S.C. 154(b) by 0 days.

(21) Appl. No.: 15/482,831

(22) Filed: Apr. 10, 2017

(65) Prior Publication Data

US 2017/0322154 A1 Nov. 9, 2017

(30) Foreign Application Priority Data

May 4, 2016 (DE) ........................ 10 2016 207 759

(51) Int. Cl.
*G01N 21/64* (2006.01)
*B60Q 11/00* (2006.01)
(Continued)

(52) U.S. Cl.
CPC ....... *G01N 21/6445* (2013.01); *B60Q 11/005* (2013.01); *F21S 41/14* (2018.01);
(Continued)

(58) Field of Classification Search
CPC ........ B60Q 1/04; B60Q 11/00; B60Q 11/005; F21K 9/64; F21S 41/14; F21S 41/147;
(Continued)

(56) References Cited

U.S. PATENT DOCUMENTS 5,471,515 A * 11/1995 Fossum ................ G11C 19/282
377/60
8,400,011 B2   3/2013 Kawaguchi et al.
(Continued)

FOREIGN PATENT DOCUMENTS

DE   102012220481 A1   5/2014
DE   202015001682 U1   3/2015
(Continued)

OTHER PUBLICATIONS

"Benefits of Sapphire Optics." Guild Optical Associates, 2014, www.guildoptics.com/sapphire-properties/benefits-of-sapphire-optics/. (Year: 2014).*
(Continued)

*Primary Examiner* — Alexander H Taningco
*Assistant Examiner* — Renan Luque

(57) ABSTRACT

A method for detecting damage to a converter device of a lighting apparatus is provided. The method may include irradiating the converter device with input light, detecting a useful light portion emitted principally by a first section of the converter device by means of a first sensor element. A first detection signal is obtained, detecting a useful light portion emitted principally by a second section of the converter device, said second section being different than the first section, by means of a second sensor element. A second detection signal is obtained. The method further may include automatically obtaining damage information about the converter device from a ratio or a difference of the first detection signal with respect to either the second detection signal or a comparison signal formed therefrom.

13 Claims, 4 Drawing Sheets

(51) Int. Cl.
  *G01N 21/95*  (2006.01)
  *F21S 41/14*  (2018.01)
  *F21S 41/16*  (2018.01)
  *F21S 45/70*  (2018.01)
  *G02B 27/28*  (2006.01)
  *B60Q 1/04*  (2006.01)
  *F21Y 115/30*  (2016.01)
  *G01N 21/88*  (2006.01)

(52) U.S. Cl.
  CPC ............... *F21S 41/16* (2018.01); *F21S 45/70* (2018.01); *G01N 21/95* (2013.01); *G02B 27/28* (2013.01); *B60Q 1/04* (2013.01); *F21Y 2115/30* (2016.08); *G01N 2021/646* (2013.01); *G01N 2021/8845* (2013.01); *G01N 2021/9511* (2013.01)

(58) Field of Classification Search
  CPC .......... F21S 41/16; F21S 41/25; F21S 41/255; F21S 41/285; F21S 41/32; F21S 41/37; F21S 41/39; F21S 41/675; F21S 43/00; F21S 45/00; F21S 48/1145; F21S 48/1159; F21S 48/1225; F21V 23/00; F21V 23/0457; F21V 25/00; F21V 25/02; F21V 25/04; F21Y 2115/30; G01J 1/42; G01J 2001/4247; G01J 3/505; G01M 11/0285; G02B 26/10; G02B 5/02; G02B 5/32; G03B 21/204; G03B 21/2066; G03B 21/208; H01S 3/0078; H01S 5/005; H01S 5/022; H01S 5/02296; H01S 5/06808; H01S 5/06825; H01S 5/0683
  See application file for complete search history.

(56) References Cited

U.S. PATENT DOCUMENTS

| | | | |
|---|---|---|---|
| 2003/0123705 A1* | 7/2003 | Stam | B60Q 1/085 382/104 |
| 2008/0137042 A1* | 6/2008 | Alasaarela | G02B 27/0927 353/102 |
| 2011/0116520 A1* | 5/2011 | Krijn | H01S 5/005 372/29.02 |
| 2011/0292636 A1* | 12/2011 | Fukai | F21S 41/16 362/19 |
| 2014/0085265 A1* | 3/2014 | Yin | G06F 1/1637 345/175 |
| 2015/0241709 A1* | 8/2015 | Stelzer | G01J 1/4257 359/636 |
| 2016/0290584 A1* | 10/2016 | Nomura | H01S 5/005 |
| 2016/0305626 A1* | 10/2016 | Tatara | F21S 48/1225 |
| 2017/0139096 A1* | 5/2017 | Frederiksen | G01J 1/42 |
| 2017/0267175 A1* | 9/2017 | Ichikawa | B60Q 1/04 |

FOREIGN PATENT DOCUMENTS

| | | | | |
|---|---|---|---|---|
| DE | 102014202294 A1 | 8/2015 | | |
| DE | 102014202943 A1 | 8/2015 | | |
| DE | 102014212370 A1 | 12/2015 | | |
| EP | 2119531 A1 * | 11/2009 | ............... | F16P 1/06 |
| EP | 2297827 B1 | 6/2012 | | |
| JP | 2013191479 A * | 9/2013 | ............. | F21S 41/14 |
| JP | 2013191479 A | 9/2013 | | |
| WO | 2014072226 A1 | 5/2014 | | |
| WO | WO 2014072226 A1 * | 5/2014 | .......... | B60Q 1/0023 |
| WO | 2015118003 A1 | 8/2015 | | |
| WO | 2015124428 A1 | 8/2015 | | |

OTHER PUBLICATIONS

German Search Report based on application No. 10 2016 207 759.7 (8 pages) dated Apr. 12, 2017 (Reference Purpose Only).

* cited by examiner

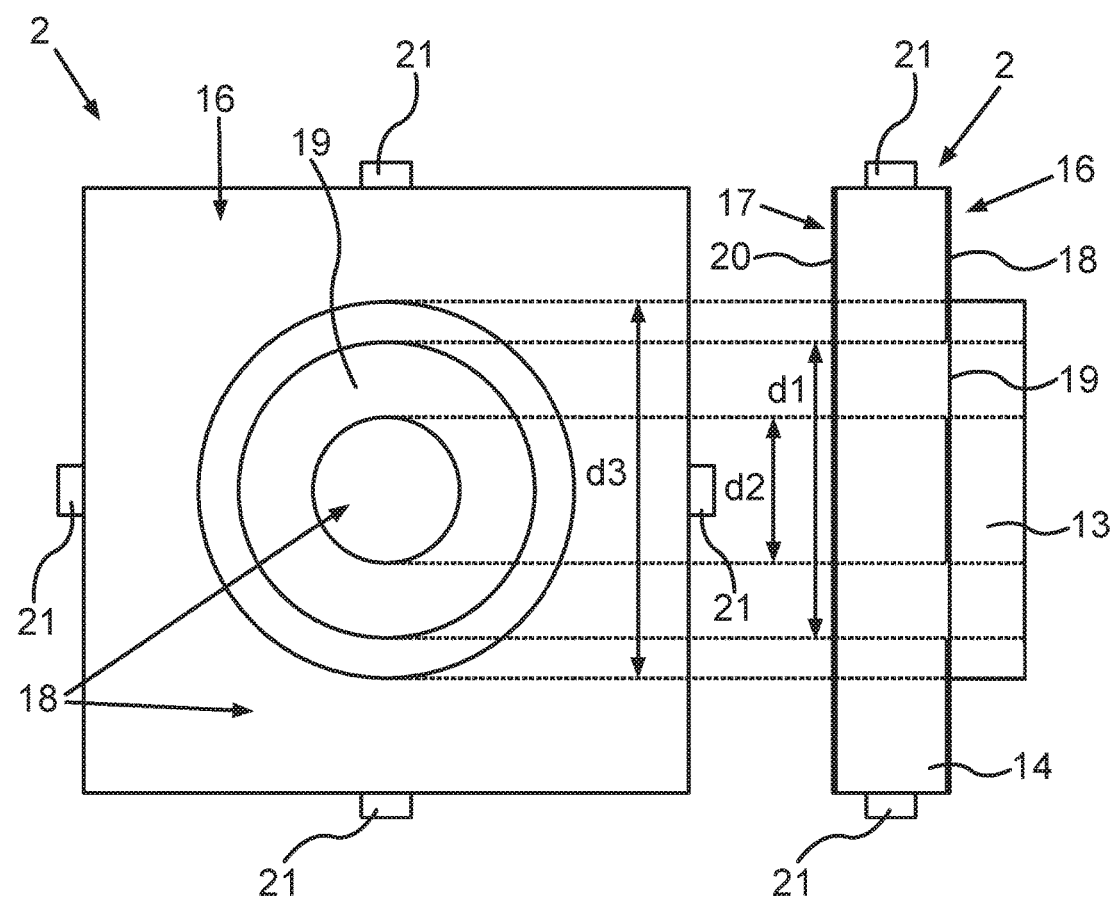

DETECTING DAMAGE TO A CONVERTER DEVICE

CROSS-REFERENCE TO RELATED APPLICATION

This application claims priority to German Patent Application Serial No. 10 2016 207 759.7, which was filed May 4, 2016, and is incorporated herein by reference in its entirety.

TECHNICAL FIELD

Various embodiments relate generally to a method for detecting damage to a converter device of a lighting apparatus. Furthermore, various embodiments relate to a corresponding lighting apparatus having a light source and a converter device, which is irradiated with input light by the light source during operation, for generating useful light.

BACKGROUND

A lighting apparatus usually includes a laser as light source, for example, the radiation of which laser is directed onto a converter including phosphor, for example. The laser used generates blue light, for example, and the converter converts said blue light partly into yellow light. Such a lighting apparatus is referred to as LARP system (Laser Activated Remote Phosphor), for example. Specifically, it is possible to use such lighting apparatuses as module constructed in the automotive sector as motor vehicle headlight.

The optical safety monitoring of LARP modules, wherein for example a partially defective converter is intended to be detected, involves carrying out, for example, a measurement of the ratio of yellow light to blue light in the useful light. In this case, it is difficult to define a threshold value for the detection of a fault case. Causes of these difficulties are, inter alia, the fact that said ratio also changes if the power density at the converter or the temperature changes. This is because both parameters change the conversion efficiency of the converter and thus the yellow/blue ratio. Moreover, the surfaces in the optical path of the sensor signal may change in a wavelength-dependent manner during the lifetime. In addition, the efficiency of the converter may change over the lifetime.

The document EP 2 297 827 B1 discloses a method for operating a laser-based light source. At least part of the laser light is converted into converted light. A signal for the converted light which is related to the power of the emitted laser light is determined. A parameter safe for operation is determined on the basis of the laser output signal and the signal for the converted light. The parameter safe for operation is compared with at least one threshold value defined beforehand. Finally, the operation of the laser-based light source is controlled on the basis of the comparison of the parameter safe for operation with the threshold value defined beforehand.

Moreover, the document U.S. Pat. No. 8,400,011 B2 describes a lighting apparatus having improved safety visa vis the human eye. The lighting apparatus may be used for motor vehicles. A fluorescent plate is irradiated with the laser light and part of the laser light is reflected. This reflected part of the light is detected and used for the control of the laser.

Furthermore, the document DE 20 2015 01 682 U1 discloses a lighting device for a vehicle including a laser diode arrangement, a light wavelength conversion element for the wavelength conversion of the light generated by the laser diode arrangement, and also a safety apparatus for measuring a fault case of the light wavelength conversion element. The safety apparatus includes at least one signal transmitter and at least one signal receiver for transmitting and receiving measurement radiation. The at least one signal transmitter and the at least one signal receiver are arranged on different sides of the light wavelength conversion element, such that measurement radiation from at least one signal transmitter penetrates through the light wavelength conversion element.

In order to avoid the abovementioned problem of difficult fault detection when monitoring e.g. the yellow/blue ratio, often a beam trap is additionally used. In the fault case, the blue laser light is absorbed there. Said beam trap considerably reduces the useful luminous flux.

SUMMARY

A method for detecting damage to a converter device of a lighting apparatus is provided. The method may include irradiating the converter device with input light, detecting a useful light portion emitted principally by a first section of the converter device by means of a first sensor element. A first detection signal is obtained, detecting a useful light portion emitted principally by a second section of the converter device, said second section being different than the first section, by means of a second sensor element. A second detection signal is obtained. The method further may include automatically obtaining damage information about the converter device from a ratio or a difference of the first detection signal with respect to either the second detection signal or a comparison signal formed therefrom.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 6 shows a plan view of a converter device with sensor elements;

FIG. 7 shows an end-side view of the converter device with sensor elements in accordance with FIG. 6;

DESCRIPTION

Figure 1:
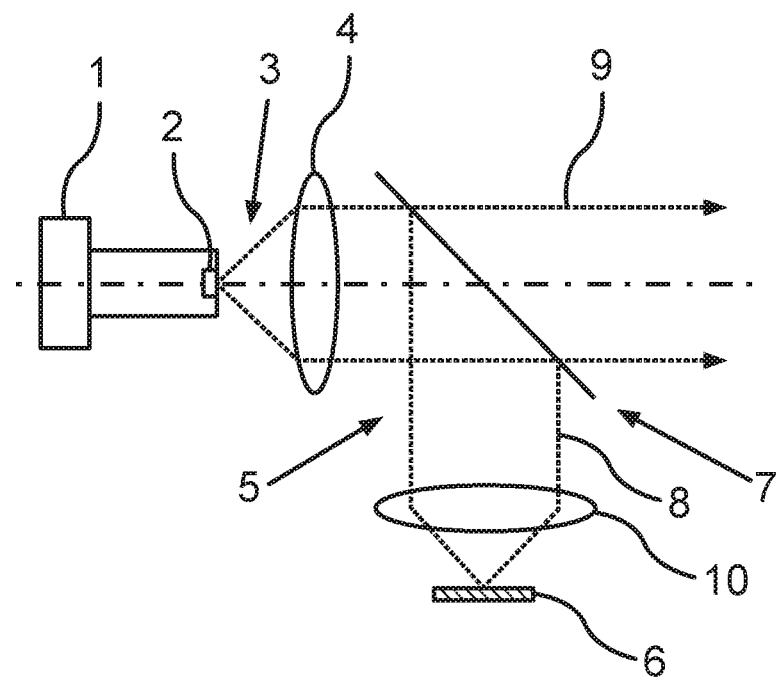
FIG. 1 shows the set-up of a lighting apparatus according to various embodiments.

The following detailed description refers to the accompanying drawings that show, by way of illustration, specific details and embodiments in which the invention may be practiced.

The embodiments outlined in greater detail below represent various embodiments. It should be taken into consideration here that the individual features can be realized not only in their outlined feature combinations, but also by themselves or in other technically expedient combinations.

Various embodiments, in the case of a lighting apparatus in which input light is converted into useful light by a converter device, are able to identify damage to the converter device more reliably.

In accordance with various embodiments, accordingly a method for detecting damage to a converter device of a lighting apparatus is provided. The converter device is irradiated with input light, which is generated for example by a laser or some other light source. By way of example, the input light is blue laser light. Afterward, any useful light portion emitted principally by a first section of the converter device is detected by means of a first sensor element, wherein a first detection signal is obtained. The useful light consists of a mixture of the input light and a converted light. During the conversion, the wavelength of the light generally changes. In this regard, by way of example, by means of a converter device containing phosphor, blue light is converted into yellow light. In total, the yellow light together with the blue light, given a suitable ratio, yields white useful light. In the case of damage to the converter device, the ratio between input light and converted light is changed relative to the normal case, such that as a general rule white light no longer arises. From the useful light a portion may be coupled out for measurement purposes.

In order not to have to rely on a single detection signal for the monitoring of the converter device, in the method according to various embodiments, a useful light portion emitted principally by a second section of the converter device, said second section being different than the first section, is detected by means of a second sensor element, wherein a second detection signal is obtained. Two detection signals with respect to spatially different sections of the converter device are thus available for the further signal processing. In this case, it may be provided that the two portions of the useful light emitted by the converter device have covered approximately the same or a similar optical path, in order that they are more likely to be comparable.

The method according to various embodiments subsequently involves automatically obtaining damage information about the converter device from a ratio or a difference of the first detection signal with respect to either the second detection signal or a comparison signal formed therefrom. Thus, possible damage to the converter device is not deduced from a single detection signal for example in comparison with a predefined threshold value. Rather, at least two detection signals from different sections of the converter device are obtained and conclusions about damage to the converter device are drawn from a ratio or a difference of the two detection signals or of corresponding further-processed signals obtained therefrom (i.e. comparison signals). A spatially resolved relative variable is thus used in order to be able to make a statement about damage, rather than a single absolute variable, as is the case in the prior art.

In one embodiment, by means of at least one third sensor element, a third useful light portion emitted principally by a third section of the converter device, said third section being different than the other sections, is detected with a third detection signal being obtained and the comparison signal, e.g. an average value, is formed from the detection signals. Therefore, at least three location-related detection signals are present which form the basis for a decision regarding damage to the converter device. In this case, it may be provided that an average value is formed from the plurality of detection signals, said average value being used as a comparison signal. Current detection signals are then compared with said comparison signal and damage to the converter device is deduced depending on the comparison.

Location data of the sensor elements may be taken into account during the process of automatically obtaining, such that the damage information is location-dependent. In this case, if for example the converter area of the converter device is imaged onto the sensor elements, then faults or instances of damage of the converter device are also imaged onto the corresponding sensor elements. If the individual sensor elements are then evaluated separately by themselves and their coordinates are known, the actual location of damage on the converter device can be deduced. Therefore, it is possible to ascertain not only that damage is present, but also where damage is present.

Furthermore, each sensor element in each case may include a first and a second sensor component and a first wavelength or a first wavelength range may be detectable by means of the first sensor component and a second wavelength or wavelength range of the useful light, said second wavelength or wavelength range being different than the first wavelength, may be detectable by means of a second sensor component. Therefore, by way of example, if the first sensor component detects blue light and the second sensor component detects yellow light, a local converter efficiency may thus be inferred from the ratio of the two wavelengths. Said converter efficiency may be determined, if appropriate, in a spatially resolved manner for further sensor elements.

Alternatively, a polarization of the useful light portion, said polarization being different than a polarization of the input light, may also be detectable by means of each sensor element. This is because if the polarization changes upon the scattering of the input light, the signal strength of the light having changed polarization may be used as a measure of the conversion efficiency of the converter device.

Various embodiments provide a lighting apparatus including a light source and a converter device, which is irradiated with input light by the light source during operation, for generating useful light. In this case, the lighting apparatus includes a first sensor element for detecting a useful light portion emitted principally by a first section of the converter device, wherein a first detection signal is obtained, and a second sensor element for detecting a useful light portion emitted principally by a second section of the converter device, said second section being different than the first section, wherein a second detection signal is obtained. A signal processing device of the lighting apparatus serves for automatically obtaining damage information about the converter device from a ratio or a difference of the first detection signal with respect to either the second detection signal or a comparison signal formed therefrom. Variations of this lighting apparatus correspond to those of the method according to various embodiments. Moreover, the developments of the method as outlined above may be regarded as functional features of the lighting apparatus according to various embodiments.

Specifically, the first sensor element and the second sensor element may be in each case part of a common sensor array. In this regard, by way of example, the surface of the converter device may be imaged onto a two-dimensional sensor array. A two-dimensional image of the surface of the converter device can be obtained as a result. In various embodiments, the conversion efficiency of the converter device may thus be determined pixel by pixel. Very accurate spatially resolved information about damage to a converter device can thus be obtained using a sensor array.

A separate optical device may be arranged between the converter device and the sensor device in order to image a part of the useful light onto the sensor array. Said optical device may include a beam splitter in order to couple out part of the useful light (useful light portion). Moreover, the optical device may also include one or more lenses in order to image the surface of the converter device exactly onto the surface of the sensor array, as a result of which a high spatial resolution may be achieved. Instead of an objective (a plurality of lenses), by way of example a fiber bundle may also be used in order to achieve the imaging.

Furthermore, a converter element of the converter device may be fixed to a carrier device for the purpose of heat dissipation, the carrier device may include a transparent plate through which the input light is incident on the converter element, and the sensor elements may be arranged on end sides of the transparent plate. Such a transparent plate thus fulfills two further functions besides the carrying function, namely that of heat dissipation and that of light guiding in particular of the converted light, which is emitted isotropically upon the conversion within the converter element, to the sensor elements. The converted light may be guided for example by total internal reflection within the transparent plate to the end sides. Such a set-up including the transparent plate may be provided for reflection systems and also for transmission systems, i.e. if the input light (e.g. pump light of a laser) is reflected at the converter device or radiates through the latter.

The transparent plate for dissipating heat and for carrying the converter device may be formed from sapphire. Sapphire may be highly transparent and simultaneously has a high thermal conductivity. Therefore, it is particularly suitable as carrier material for the converter device. Alternatively, diamond could also be used for this purpose. Glass, by contrast, is less suitable since it has a comparatively low thermal conductivity.

In one specific embodiment, the transparent plate may include, on its first main side facing the light source, a first dichroic mirror (or dichroic coating), which is transmissive for the input light and reflective for light converted by the converter element. This may have the effect that in a transmission system the input light can be radiated through the transparent plate onto the converter element, whereas the converted light emitted by the converter element in the direction of the input radiation can at the latest be reflected at the dichroic mirror and thus kept better within the transparent plate. In various embodiments, here an antireflection coating is provided on the first main side.

In one development, the transparent plate may include, on its second main side facing the converter element and situated opposite the first main side, a second dichroic mirror (or dichroic coating), which is transmissive for the input light and reflective for light converted by the converter element, wherein the second dichroic mirror has a cutout through which, during operation, part of the converted light penetrates into the transparent plate and is guided to the sensor elements. The second dichroic mirror thus has the effect that the input light or pump light may also pass through again without being obstructed, while the converted light is reflected. By means of the second mirror, therefore, the light converted in the converter element is reflected back into the converter element and it can penetrate into the transparent plate only in the region of the cutout. The quantity of converted light which is intended to be guided to the sensor elements can be controlled accurately in this way.

In various embodiments, the cutout is ring-shaped and is completely covered by the converter element. This means that a part of the second dichroic mirror is arranged in the center of the ring. This may have the effect that in the center, where the most input light (e.g. blue light) passes through without being converted, the entire converted radiation (e.g. yellow light) is also reflected. In total, this results in a high light intensity of the useful light of the desired wavelength mixture (e.g. white light). Around the center, where less non-converted light emerges, the proportion of converted light is reduced by the cutout since the converted light can penetrate into the transparent plate through the cutout counter to the direction of incidence. Thus, by way of example, the yellow portion is reduced in the edge region around the center, as a result of which the effect of a yellow corona around the center can be minimized.

The converter element may include a ceramic plate, a silicone matrix or the like including phosphor. Such a ceramic plate is in particular thermally very robust. As phosphor, it is possible to use Ce-doped YAG, for example, in order to convert blue light into yellow light.

In one application, the lighting apparatus outlined above may be used in a motor vehicle headlight. Such a motor vehicle headlight may include a front sheet (e.g. intermediate light sheet or covering sheet), wherein a section of the front sheet as beam splitter is part of the optical device. In this embodiment, a motor vehicle headlight may be formed whose converter device may be reliably monitored. Alternatively, however, the lighting apparatus according to various embodiments may also be used for other headlights/spotlights and lighting systems. In this regard, the lighting apparatus may also be used for illuminating spaces, buildings, installations and the like.

Various embodiments provide a method for detecting damage to a converter device of a lighting apparatus, by
 irradiating the converter device with input light,
 detecting a polarization of a useful light portion emitted by the converter device, wherein a detection signal is obtained,
 automatically obtaining damage information about the converter device from the detection signal.

Damage to the converter device may thus be deduced on the basis of the portion or the intensity of specifically polarized light in the useful light. If appropriate, also from the useful light portion a further polarization may be detected by a further sensor element and a corresponding further detection signal may be obtained, and the further detection signal may also be used for automatically obtaining the damage information. In this regard, a conclusion about damage to the converter device may be drawn for example from a ratio of s-polarized light and p-polarized light. If spatial resolution of the statement about damage is desired, polarization signals may be determined separately for a corresponding number of sections of the converter device, as has been presented in the other method variants above.

The developments and effects outlined above in association with the lighting apparatus may, if appropriate, also be used for the method according to various embodiments, and vice versa.

For safety reasons it is necessary to monitor lighting apparatuses whose light rays might cause injuries to persons during operation, and in particular during faulty operation. In this regard, it is specifically necessary constantly to check a converter or a converter device that converts pump light (also called input light hereinafter) of a laser system, for example, into white light or else differently colored light. To that end various possibilities are described below as to how a fault of a converter device can be better identified on the basis of sensor signals. What all the solutions have in common is that at least two location-related sensor signals are used. What may thus be achieved is that power changes and temperature fluctuations do not play a (major) part with regard to fault detection. This is achieved by means of a monitoring—which is spatially resolved in the broadest sense—of the emitted light. Frequencies and/or polarizations may be monitored in this case. Possible damage to the converter device may arise as a result of fracture, age, temperature exceedance for example owing to an excessively high laser diode current, etc.

FIG. 1 shows a lighting apparatus such as may typically be used for a motor vehicle headlight. However, such a lighting apparatus may also be used for other, e.g. laser-operated, headlights/spotlights for illuminating spaces, buildings, installations and the like.

The lighting apparatus illustrated schematically in FIG. 1 has a light source 1. The latter may be for example a laser, and in particular a diode laser. The latter emits blue light.

The lighting apparatus additionally includes a converter device 2, which is irradiated by the light of the light source 1. With regard to the converter device 2, the light of the light source is also referred to as input light hereinafter. The converter device 2 converts the input light partly into converted light.

The converted light together with that part of the input light which is not converted forms the output light of the converter, which is also referred to as useful light 3 hereinafter. The converted light is emitted by the converter device 2 generally in a lambertian manner. Therefore, an optical unit, and in particular a collimator 4, may be necessary in order to obtain a parallel radiation beam of the useful light 3. From the concentrated useful light 3 or else, if appropriate, before the concentration, here an optical device 5 deflects part of the useful light (i.e. useful light portion) onto a sensor device 6. The optical device 5 has a beam splitter 7 as essential element. Said beam splitter 7 branches off part of the parallel-concentrated useful light 3. This branched-off part of the useful light may be referred to as monitoring light 8. The remaining part of the useful light 3 is referred to as residual useful light 9. In one embodiment, a beam splitter covers only a region, e.g. the central region, of the useful light.

The monitoring light 8 is focused here onto the sensor device 6 by a lens 10. Such a lens 10 need not be present, however. It is expedient particularly if a high spatial resolution is demanded.

The sensor device 6 may be designed as a sensor array. In various embodiments, a two-dimensional sensor array may be involved. The surface of the converter device 2 or the surface of a corresponding converter element can thus be detected two-dimensionally with pixel accuracy in accordance with the resolution of the sensor array. An image of the converter device 2 thus arises with the sensor device 6. However, the sensor device 6 may also be equipped with fewer sensor elements. At the very least two sensor elements must be provided in order to be able to capture the light of different sections of the converter device.

The converter is thus imaged onto the sensor array for example with ten-fold magnification. A spatially resolved detection of faults or defects of the converter element (e.g. converter lamina) is thus possible. The sensor array of the sensor device 6 measures or determines the color of the light or at least for example the ratio of blue light to yellow light. If a piece of the converter is absent, the yellow-blue ratio changes at the imaged location of the hole. Spatial differences in the useful light arise on account of these local differences in the converter efficiency. In various embodiments, a first part of the useful light may be assigned to a first local section of the converter device and a second part of the useful light, said second part being different than the first part, may be assigned to a second local section of the converter device.

In known systems with integral measurement of yellow with respect to blue, the corresponding signal magnitude or signal difference is often very small because power and temperature changes and also surface changes likewise change the yellow-to-blue ratio. In the case of the above-described spatially resolved measurement in which a first detection signal results principally from a first section of the converter device and a second detection signal results principally from a second section of the converter device, there is the possibility of evaluating only that light which comes from the defective region. Consequently, intermixing with the light from the still intact regions of the converter does not take place. This results in an increase in the signal-to-noise ratio of the defect signal in relation to a normal signal.

In the evaluation of the pixels of the sensor array, it is always possible to subtract the average value of all the pixels from each individual value. The effect of power and temperature fluctuations can be excluded computationally in this way. The fault case where the entire converter fails may additionally be monitored by observing absolute changes in the yellow-blue ratio of all the pixels.

Figure 2:
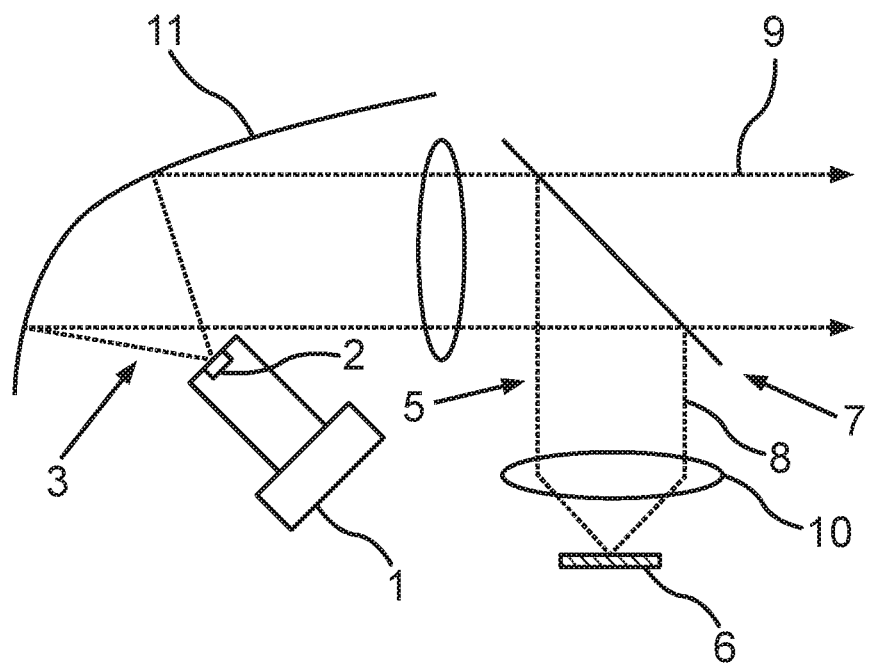
FIG. 2 shows a lighting apparatus according to various embodiments integrated into a vehicle headlight.

FIG. 2 schematically illustrates a variant of the lighting apparatus from FIG. 1. Instead of the collimator 4, a reflector 11 such as can often be found in a motor vehicle headlight is used here for generating a parallel beam of rays of the useful light 3. The similar effect of collimator 4 and reflector 11 results in the same functioning for the lighting apparatus as in the example from FIG. 1.

Figure 3:
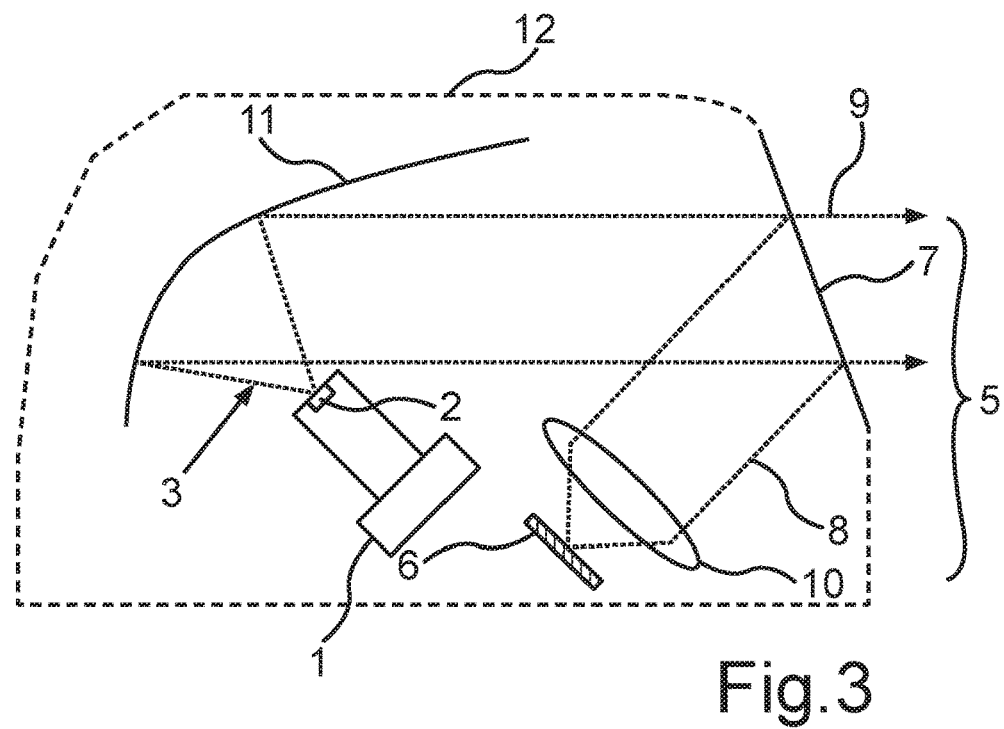
FIG. 3 shows a variant of the headlight from FIG. 2.

A further embodiment variant is represented in FIG. 3. This variant constitutes a development of the embodiment from FIG. 2. The lighting apparatus is situated in a headlight housing 12. The headlight housing has a front sheet, which here fulfills the function of the beam splitter 7. The front sheet is thus simultaneously part of the optical device 5, which also includes, if appropriate, the lens 10 or other optical components. With regard to the function, reference is once again made to the description of FIG. 1.

Figure 4:
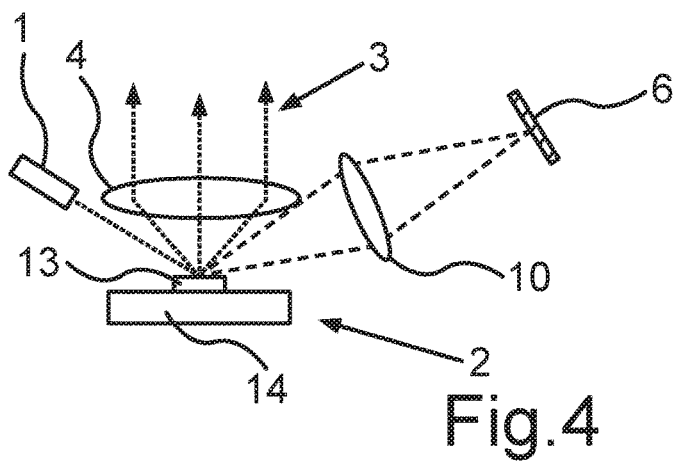
FIG. 4 shows a reflective system according to various embodiments.
Figure 5:
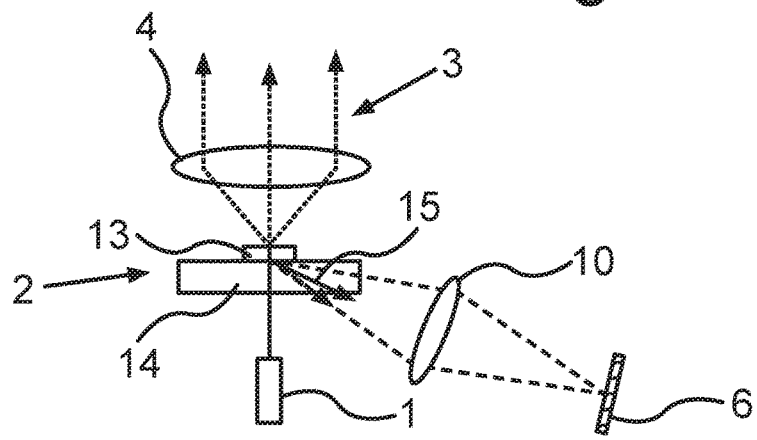
FIG. 5 shows a transmissive system according to various embodiments.

FIG. 4 and FIG. 5 show basic variation possibilities for a lighting apparatus with spatially resolved converter monitoring. A converter device 2 has a converter lamina or converter element 13, which is arranged on a heat sink 14. In various embodiments, besides the cooling function, said heat sink 14 additionally has a carrier function and, if appropriate, optical properties, such as e.g. reflective properties. The converter element 13 is irradiated with the light of a light source 1. The useful light 3 emitted by the converter element 13 is concentrated here by a collimator 4, for example. Part of the light of the light source 1 (e.g. blue laser light) is reflected directly from the converter element 13 in the direction of a sensor device 6. If appropriate, here as well an objective 10 is interposed. Part of the converted radiation, which after all is emitted in a lambertian manner, also reaches the sensor device 6. Since, here as well, the surface of the converter element 13 is imaged onto the sensor device 6, which may be designed as a sensor array, the converter element can be monitored in a spatially resolved manner, as in the embodiments previously. The example from FIG. 4 thus shows a variant with reflective pumping of the converter.

FIG. 5, by contrast, shows a variant with transmissive pumping of the converter. The light source 1 thus radiates through the heat sink 14 and the converter element 13. The carrier element or the heat sink 14 (e.g. composed of sapphire) is provided here with a dichroic mirror. However, the latter is not ideal and part of the converted light (cf. arrow 15) is also transmitted toward the rear or through the heat sink 14. Pump light (e.g. blue light) is also scattered partly toward the rear by the converter element 13. In this way, the yellow-blue ratio can be monitored in a spatially resolved manner. It may be provided that the objective 10 realizes a magnified imaging (e.g. 1:10) of the converter element 13 onto the sensor device 6.

FIG. 6 shows one specific form of a converter device 2. FIG. 6 represents a plan view, while FIG. 7 represents a side view of the converter device 2. As in the previous examples, the converter device 2 includes a heat sink 14, which may be designed for example in a laminar or parallelepipedal fashion. Said heat sink is formed from sapphire, for example. Sapphire has a high thermal conductivity and may be transparent to the pump light and the converted light. The laminar heat sink 14, which is also referred to as transparent plate in the present document, has a first main side 17 and an opposite, second main side 16. The second main side 16 is coated here with a second dichroic mirror 18. In the present example, the second dichroic mirror 18 covers the entire main side 16 with the exception of a ring 19 having an external diameter d1 and an internal diameter d2. The converter element 13 designed here in a disk-shaped fashion, is situated on the second main side 16 or the second dichroic mirror 18 with the ring 19. Said converter element has a diameter d3 that is greater than the external diameter d1 of the ring 19. The complete ring 19 is thus covered by the converter element 13.

In the present example, the first main side 17 of the heat sink 14 is provided completely with a first dichroic mirror 20. Said dichroic mirror is transmissive for the pump light (e.g. blue light) and reflective for the converted light (e.g. yellow light). The same applies to the second dichroic mirror 18. The first main side may also have an antireflection coating or no coating at all. However, only propagation via total internal reflection within the heat sink 14 toward the sensors is possible in that case.

At least two sensor elements 21 are provided on the end sides of the heat sink 14 which are perpendicular to the main sides 16 and 17. In various embodiments, at least two such sensor elements are situated on opposite end sides of the heat sink 14. In the example in FIG. 6, a respective sensor element 21 is situated on each of the four end sides of the laminar heat sink 14.

The functioning of the converter device in FIG. 6 and FIG. 7 will now be explained in greater detail in conjunction with FIG. 8. The input light or pump light 22 of a light source not illustrated here (e.g. blue laser light) is directed through the transparent heat sink 14 onto the converter element 13. In the process it penetrates through both the first dichroic mirror 20 and the second dichroic mirror 18. In the converter element 13, it partly impinges on phosphor particles 23. It is converted by the latter for example into yellow light, emitted isotropically in this case and emitted from the converter element 13 in a lambertian manner e.g. in accordance with the arrows 24 in the direction of the pump light 22 (that is to say toward the right in accordance with arrow 27 in FIG. 8).

From other phosphor particles 23, the light is firstly emitted onto the second dichroic mirror 18 and there is emitted from the converter element 13 in accordance with arrow 25 once again for instance in the direction of the pump light (that is to say once again toward the right). Other portions of the pump light 22 pass through the converter element 13 without impinging on a phosphor particle 23, for which reason they are not converted into a different frequency. They are scattered in the converter element 13 and leave the latter for example in the direction in accordance with arrow 26.

Some of the photons of the pump light 22 which impinge on phosphor particles 23 are converted and lead to a light radiation in the direction of the heat sink 14, in a manner similar to that in the case of arrow 25. In the region of the ring 29, however, in which the second dichroic mirror 18 has a cutout, this radiation directed backward is directed into the heat sink 14 and directed there either by total internal reflection or by means of the first and second dichroic mirrors 18, 20 to one of the end sides of the heat sink 14 and impinges there on one of the sensors 21.

In the case of symmetrical irradiation, each of the sensors 21 takes up approximately the same intensity of converted radiation. If the converter element 13 is damaged in one section, however, the closest sensor will take up less converted radiation. By comparing the detection signals of the individual sensors 21, it is then possible to determine in what region for instance the converter element 13 is damaged.

What is much more important, however, is that it is actually possible to determine more reliably that the converter element 13 is damaged, since the sensor(s) 21 affected to a lesser extent by the damage supply/supplies a reference value with which other influences, such as aging, temperature and the like, can be eliminated. Specifically, if the individual detection signals deviate greatly from one another, then this is a reliable indication that the converter element 13 is damaged. This deviation can be determined by difference or quotient, for example.

The specific shape of the ring-shaped cutout 19 of the second dichroic mirror 18, besides admitting the converted radiation into the heat sink 14, has the purpose that in the circular central region, in which the major part of the pump light 22 impinges, more converted radiation is directed toward the front in the useful light direction 27, which is shown by arrow 25. Rather bluish-white light is thus emitted in the center 28 of the converter. From the edge regions 29 and 30, by contrast, less blue pump light is scattered in accordance with arrow 26, such that here it is also expedient if less converted radiation is reflected there on account of the cutout 19. Thus, the edge regions also become rather white and a yellow corona that is otherwise customary is avoided or reduced. Consequently, on the output side it is also possible to dispense with a diaphragm that masks out a yellow corona.

Figure 8:
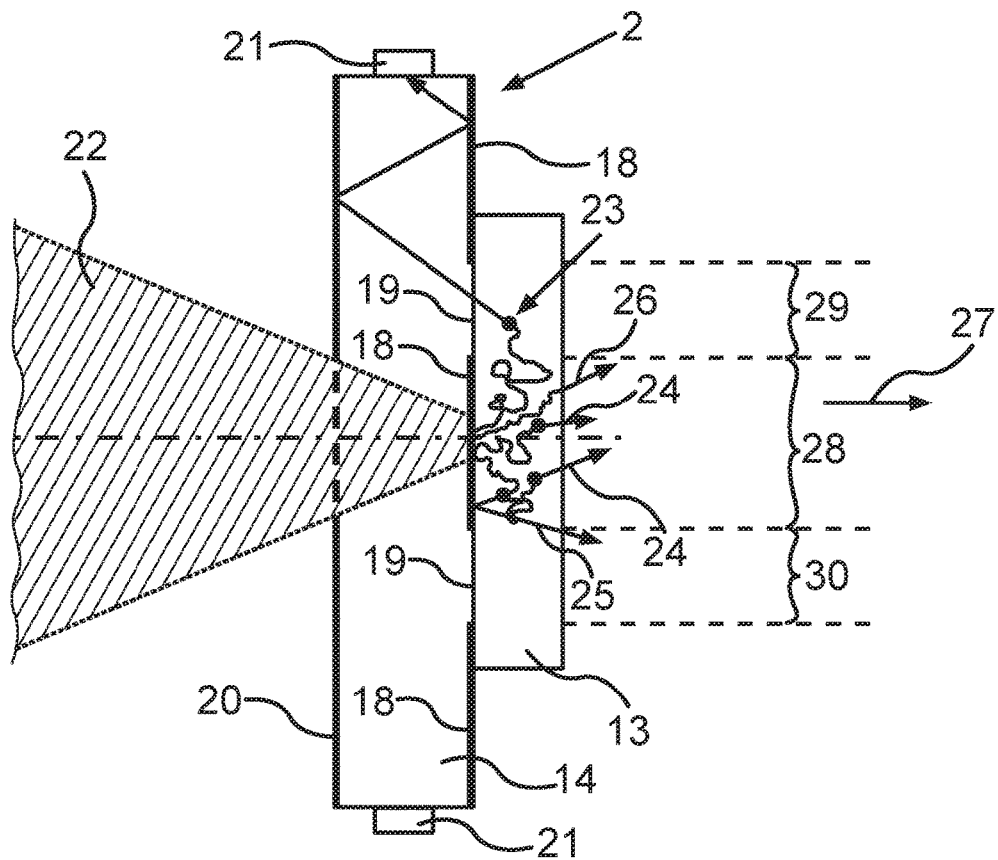
FIG. 8 shows the end-side view from FIG. 7 during operation.

In one variant indicated in FIG. 8, the second dichroic mirror or the dichroic layer may be omitted in the region of the entrance of the pump light 22 into the heat sink 14.

Thus, whereas in conventional solutions signal changes on account of instances of damage to the converter element turn out to be only very small, the concept with a structured dichroic layer affords the effect that, in a manner similar to the concept in accordance with FIG. 1 with a plurality of sensors or a sensor array, the average values of all the sensors may also be subtracted from the signal of each individual sensor. The system is thus likewise insensitive to temperature fluctuations and power fluctuations.

Figure 9:
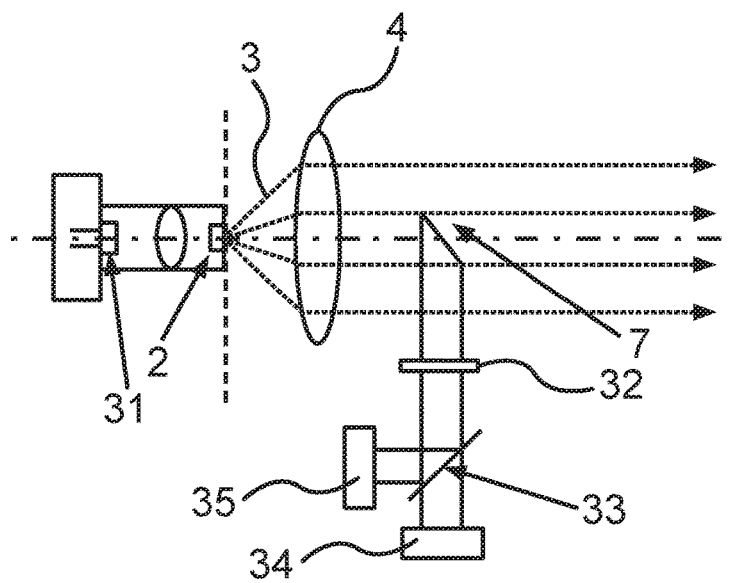
FIG. 9 shows a lighting apparatus according to various embodiments with detection of polarization differences.

A further embodiment is illustrated in FIG. 9. A laser diode 31 as light source emits for example p-polarized light to the converter device 2 (p-pol). In normal operation, the polarization direction is rotated in the case of part of the e.g.

blue light of the laser diode 31 upon passage through the converter device 2. This is carried out for example by means of scattering in the converter ceramic. Useful light having a p-polarization and an s-polarization (p+s-pol) thus arises. Here, too, a collimator 4 may concentrate the useful light 3.

A small part of the blue light is coupled out from the useful light 3 by a beam splitter 7. By way of example, a blue filter 32 serves to exclude converted light from the coupled-out light. The signal-to-noise ratio can be increased as a result. It suffices to couple out the angle range which the pump radiation or blue radiation has in the fault case without a converter 2. Said coupled-out light is then decomposed into its portions for example by a dichroic mirror 33. The latter acts for example in a transmissive fashion for p-polarized portions and in a reflective fashion for s-polarized portions. Accordingly, a detector 34 serves for detecting the p-polarized portions and a second detector 35 serves for detecting the s-polarized portions. The ratio s/p can be formed from the two detection signals. Said ratio changes in the fault case, i.e. if the converter is absent or acquires holes. This is because in the fault case the blue light passes through the hole in the converter without being scattered and maintains its original polarization.

For an optionally spatially resolved measurement, it is possible to obtain polarization portions from a plurality of sections of the converter in the above manner. If appropriate, it also suffices to detect only in each case s-polarized portions from different sections of the converter device.

In the conventional evaluation of the yellow-to-blue ratio for fault detection, the problem exists that the materials in the optical path of the measurement signal age in a wavelength-dependent manner, that is to say that the yellow-to-blue ratio may also change as a result of aging. Since the efficiency of the converter is temperature- and power-dependent, the yellow-to-blue ratio also changes depending on the operating state. These problems are eliminated in the embodiment from FIG. 9 because only the ratio s/p of the blue light is taken into consideration.

LIST OF REFERENCE SIGNS

Light source 1
Converter device 2
Useful light 3
Collimator 4
Optical device 5
Sensor device 6
Beam splitter 7
Monitoring light 8
Residual useful light 9
Lens 10
Reflector 11
Headlight housing 12
Converter element 13
Heat sink 14
Arrow 15
Main side 16
Main side 17
Dichroic mirror 18
Ring 19
Dichroic mirror 20
Sensor element 21
Input light or pump light 22
Phosphor particle 23
Arrow 24
Arrow 25
Arrow 26
Useful light direction 27
Center 28
Edge region 29
Edge region 30
Laser diode 31
Blue filter 32
Dichroic mirror 33
First detector 34
Second detector 35

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for detecting damage to a converter device of a lighting apparatus, the method comprising:
   irradiating the converter device with input light, wherein the converter device is arranged directly on a transparent heat sink; wherein the transparent heat sink comprises at least a first sensor element and a second sensor element arranged on end sides of the heat sink; and wherein the input light is incident on the converter device through the transparent heat sink;
   detecting a useful light portion emitted principally by a first section of the converter device by means of the first sensor element, wherein a first detection signal is obtained,
   detecting a useful light portion emitted principally by a second section of the converter device, said second section being different than the first section, by means of the second sensor element, wherein a second detection signal is obtained, and
   obtaining damage information about the converter device from a ratio or a difference of the first detection signal with respect to either the second detection signal or a comparison signal formed therefrom.

2. The method of claim 1,
   wherein, by means of at least one third sensor element, a third useful light portion emitted principally by a third section of the converter device, said third section being different than the other sections, is detected with a third detection signal being obtained and the comparison signal is formed from the detection signals.

3. The method of claim 2,
   wherein the comparison signal is an average value.

4. The method of claim 2,
   wherein location data of the sensor elements are taken into account during the process of obtaining, such that the damage information is location-dependent.

5. The method of claim 1, wherein each sensor element in each case comprises a first and a second sensor component and a first wavelength is detectable by means of the first sensor component and a second wavelength of the useful light, said second wavelength being different than the first wavelength, is detectable by means of the second sensor component.

6. A lighting apparatus, comprising:
   a light source, and
   a converter device, which is irradiated with input light by the light source during operation, for generating useful light, wherein the converter device is arranged directly on a transparent heat sink; wherein the transparent heat sink comprises at least a first sensor element and a second sensor element arranged on end sides of the converter device; and wherein the input light is incident on the converter device through the transparent heat sink;

wherein the first sensor element is configured to detect a useful light portion of the useful light emitted principally by a first section of the converter device, wherein a first detection signal is obtained, wherein the second sensor element is configured to detect a useful light portion of the useful light emitted principally by a second section of the converter device, said second section being different than the first section, wherein a second detection signal is obtained, and a signal processing device for obtaining damage information about the converter device from a ratio or a difference of the first detection signal with respect to either the second detection signal or a comparison signal formed therefrom.

7. The lighting apparatus of claim 6,
wherein the transparent heat sink is formed from sapphire.

8. The lighting apparatus of claim 6,
wherein the transparent heat sink comprises, on its first main side facing the light source, a first dichroic mirror, which is transmissive for the input light and reflective for light converted by the converter element, or an antireflection coating.

9. The lighting apparatus of claim 8,
wherein the transparent heat sink comprises, on its second main side facing the converter element and situated opposite the first main side, a second dichroic mirror, which is transmissive for the input light and reflective for light converted by the converter element, and wherein the second dichroic mirror has a cutout through which, during operation, part of the converted light penetrates into the transparent heat sink and is guided to the sensor elements.

10. The lighting apparatus of claim 9,
wherein the cutout is ring-shaped and is completely covered by the converter element.

11. The lighting apparatus of claim 6,
wherein the converter element comprises a ceramic plate or a silicone matrix comprising phosphor.

12. The method of claim 1, wherein the obtaining damage information about the converter device occurs automatically.

13. The lighting device of claim 6, wherein the obtaining damage information about the converter device occurs automatically.

* * * * *